United States Patent [19]

Dassanayake

[11] Patent Number: 4,999,374

[45] Date of Patent: Mar. 12, 1991

[54] VETERINARY TREATMENT

[76] Inventor: Lincoln Dassanayake, 15, Limes Avenue, Aylesbury, Buckinghamshire, England

[21] Appl. No.: 270,002

[22] Filed: Nov. 14, 1988

[30] Foreign Application Priority Data

Nov. 11, 1987 [GB] United Kingdom ............... 8726384

[51] Int. Cl.$^5$ .............................................. A61K 31/35
[52] U.S. Cl. .................................... 514/451; 514/459
[58] Field of Search ................................ 514/451, 459

[56] References Cited

PUBLICATIONS

Chemical Abstracts 99:158138e (1983).

Primary Examiner—Jerome D. Goldberg
Attorney, Agent, or Firm—Donald Brown

[57] ABSTRACT

The antibiotic compound M139603 (tetronasin), disclosed in GB-A-2027013 as a growth-promotant in farm animals with activity against Gram-positive bacteria, has now been found to prevent and treat Treponema hyodysenteriae infections in pigs (swine dysentery).

Analogues of M139603 have the same action.

The compound is administered in the pig's food or water supply.

3 Claims, No Drawings

VETERINARY TREATMENT

This invention relates to the treatment of *Treponema hyodysenteriae* infection in pigs, *T. hyodysenteriae* being the causative organism of swine dysentery, a debilitating, economically costly and sometimes fatal disease.

Current medicaments include ethacridine lactate, tylosin, erythromycin, tiamulin and certain polyether antibiotics such as salinomycin and lasalocid. It has now been found that the compound known as ICI M139603 or tetronasin, disclosed in GB-A-2 027 013 as being a growth-promoting antibiotic with activity against Grampositive bacteria and coccidia, has surprising levels of activity against *T.hyodysenteriae*.

Accordingly, one aspect of the invention provides the preparation of a medicament, for use in combatting or preventing *Treponema hyodysenteriae* infections in pigs, comprising the compound M139603 or physiologically functional equivalents thereof.

A second aspect provides a composition comprising M139603 or physiologically functional equivalents thereof and specifically adapted for use in combatting or preventing *Treponema hyodysenteriae* infections in pigs.

A third aspect provides a method of combatting or preventing *Treponema hyodysenteriae* infection in pigs comprising the administration to the pigs of a non-toxic, infection-combatting or infection-preventing amount of M139603 or physiologically functional equivalents thereof.

The compound M139603 is a metabolite produced by at least some strains of *Streptomyces longisporoflavus*, including the strain which is freely available as deposit NCIB 11426 from the National Collections of Industrial and Marine Bacteria, P.O. Box 31, Aberdeen, Scotland AB9 8DG and as CBL 312.79 from CBS, P.O. Box 273, 3740 Baarn, Netherlands. Its isolation and characteristics are described in GB-A-2 027 013 and in Davies et al, J.C.S. Chem. Comm., 1981, 1073-4.

The term "physiologically functional equivalents of M139603" includes the free acid (M139603 being the sodium salt), salts (especially alkali metal salts), ethers, esters, urethanes, thiourethanes, carbonates, aldehydes and oximes such as are disclosed in EP-A-70 622 (which is incorporated herein by reference) and generally all compounds having the active polyether structure of M139603 with only such modifications thereof which do not diminish its activity to an unacceptable level. The equivalent compounds are preferably compounds of Formula (I):

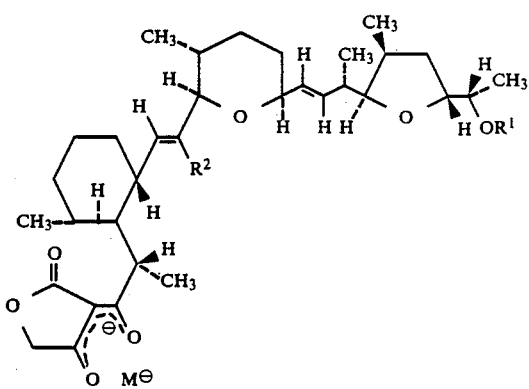

wherein:

M+ is an alkali metal, alkaline earth metal, ammonium, alkylammonium or hydroxyalkylammonium cation;

$R^1$ is a hydrogen atom, an alkyl radical or an optionally substituted phenylalkyl radical; and $R^2$ is a formyl, iminomethyl, hydroxyiminimethyl or aminomethyl radical, or a radical of the formula —CH:$NR^3$, —CH:$NOR^4$ or —$CH_2NR^5R^6$ wherein $R^3$, $R^4$, $R^5$ and $R^6$ may each be an alkyl or an optionally substituted phenyl or phenylalkyl radical; or a radical of the formula —$CH_2OR^7$ wherein R is an alkyl, alkenyl, alkynyl, alkoxycarbonyl or alkylaminoalkyl radical or an optionally substituted phenylalkyl radical; or a radical of the formula —$CH_2O.COR^8$ wherein $R^8$ is an alkyl, cycloalkyl, (cycloalkyl)alkyl, halogenoalkyl, hydroxyalkyl, alkoxyalkyl, aminoalkyl, mono- or dialkylaminoalkyl, alkoxycarbonylalkyl, carboxyalkyl, carbamoylalkyl, N-alkylcarbamoylalkyl, N,N-dialkylcarbamoylalkyl or optionally substituted phenyl, naphthyl or phenylalkyl radical; or a radical of the formula —$CH_2O.CO.COR^9$ wherein $R^9$ is an amino, mono- or di-alkylamino, alkoxy or optionally substituted phenyl, naphthyl or phenylalkyl radical; or a radical of the formula —$CH_2O.CX.NR^{10}R^{11}$ wherein X is an oxygen or sulphur atom and $R^{10}$ and $R^{11}$, which may be the same or different, are each a hydrogen atom, an alkyl radical or an optionally substituted phenyl, naphthyl or phenylalkyl radical;

or, when $R^1$ is a hydrogen atom or an alkyl radical of 2 or more carbon atoms or an optionally substituted phenylalkyl radical, $R^2$ is a hydroxymethyl radical, and wherein each alkyl, alkenyl or alkynyl radical contains up to 6 carbon atoms, and wherein, in each complex radical containing an alkyl part, the said alkyl part contains 1 to 6 carbon atoms, and wherein each cycloalkyl radical or cycloalkyl part of a (cycloalkyl)-alkyl radical contains 3 to 7 carbon atoms.

A particular value for any of $R^1$, $R^2$, $R^3$, $R^4$, $R^5$, $R^6$, $R^7$, $R^8$, $R^{10}$ and $R^{11}$ when it is an alkyl radical, or when it is a complex radical containing an alkyl part, is, for example, such an alkyl radical which contains 1 to 3 carbon atoms, or such a complex radical wherein the alkyl part contains 1 to 3 carbon atoms.

A particular optional substituent in $R^1$, $R^3$, $R^4$, $R^5$, $R^6$, $R^7$, $R^8$, $R^9$, $R^{10}$ or $R^{11}$ when any of them is an optionally substituted phenyl, naphthyl or phenylalkyl radical is, for example, a halogen atom, a nitro, cyano or hydroxy radical, or an akyl, alkoxy, halogenoalkyl, halogenalkoxy, alkylamino, dialkylamino or alkanoylamino radical, for example such a radical of up to 8 carbon atoms, preferably of up to 4 carbon atoms.

A particular value for $R^7$ when it is an alkenyl or alkynyl radical is, for example, such a radical of 2 or 3 carbon atoms.

Particular cations M+ are, for example, the sodium, lithium, potassium, calcium, magnesium, zinc, ammonium, mono-, di-, tri- and tetra-alkylammonium ions wherein each alkyl is of 1 to 10 carbon atoms, and mono-, di- and tri-(hydroxyalkyl)ammonium ions wherein each hydroxyalkyl is of 1 to 10 carbon atoms.

Particular compounds of the invention which are preferred are those compounds of Formula I wherein $R^1$ is methyl and $R^2$ is hydroxymethyl, formyl, methoxy-methyl, propargyloxymethyl, benzoyloxymethyl, 2-bromobenzoyloxymethyl, chloroacetoxymethyl, ethoxalyloxymethyl or N-methylthiocarbomoyloxymethyl.

The fifteen analogues mentioned below in Example 8 are specific Examples.

The following further examples of compounds within the scope of the invention may also be mentioned, referring to the structural formula given above, M+ being sodium and $R^1$ being methyl (except where indicated):

$R^2$

—$CH_2O.COCH_2Cl$
—$CH_2OCH_2$—(1-bromophenyl)
—$CH_2O(CH_2)_2NMe_2$
—$CH_2O.CONHPh$
—$CH_2OH$ ($R^1$ is hydrogen)

Such compounds may be made by the methods described in Ep-A-706822.

M139603 or equivalent may be administered to the pigs by any suitable route, preferably orally and especially in their normal feed or drinking water. When presented in the feed, levels as low as 10 ppm have been found to be effective. In a pig which consumes about 6% of its body weight per day under experimental conditions. (e.g. quickly growing hybrids under S.P.F. conditions), this dosage is equivalent to about 0.6 mg/kg body weight, which is very low in comparison with other compounds effective against swine dysentery. Typical food consumption rates on farms vary from 4% (40–50 kg animals) to 5% (animals up to 20 kg). In general, feed levels of 5–200 ppm of M139603 or equivalent are useful, with levels of 10–50 ppm, particularly about 15, 20, 25, 30, 35, 40, 45 or 50 ppm being preferred.

EXAMPLE 1

IN VITRO ACTIVITY

The minimum inhibitory concentration of M139603 was tested in parallel with dimetridazole (May & Baker) and the growth-promoting polyether antibiotic salinomycin (Hoechst) against thirteen strains of *T. hyodysenteriae*. The results are given in Table 1. Statistical analyses of the MIC results have shown M139603 to have a significantly ($p<0.001$) lower MIC (mean=0.215 mcg) than salinomycin (mean=0.688 mcg).

EXAMPLE 2

COMPARATIVE EFFICACY OF M139603 AND MONENS IN MICE

Young mice (strain MF-1, Olac Ltd), each weighing 20 grams approximately, given ad lib drinking-water medicated with spectinomycin hydrochloride ("Spectam", Abbotts) at a concentration of 1.25 g/liter on three continuous days before and after the oral administration of an infective dose ($0.4 \times 10^6$ cfu per mouse) of *T.hyodysenteriae*, have been found to be consistently susceptible to the infection. The infection leads to varying degrees of caecitis, the lesions of which are apparent in animals killed on or about the sixth day post-infection. Caecal specimens examined by bacteriological culture techniques applicable for enumeration of organisms reveal the presence of high populations of *T.hyodysenteriae*. This disease-model was used in experiments to compare the efficacy of M139603 with that of salinomycin, lasalocid and monensin in suppressing the infection.

In this study, the efficacy of M139603 was tested at 25 ppm feed and that of monensin (Eli Lilly) at 50 or 100 ppm. Groups of infected mice, five per group, were offered the drugs in the feed on five continuous days before killing. Caecal materials were subjected to bacteriological examination to enumerate the populations of viable treponemes per gram of material. The results are given in Table 2. Compound M139603 at 25 ppm and monensin at 100 ppm suppressed the infection but the latter drug at 50 ppm proved ineffective since four out of five animals in this group yielded high populations ($1.0 \times 10^5 - 1.7 \times 10^8$ cfu/g) of viable treponema with a group mean ($\log_{10}$) of 5.2 cfu/g caecum. The group mean in respect of the unmedicated groups was 7.9 cfu/g.

EXAMPLE 3

COMPARATIVE EFFICACY OF M139603 AND SALINOMYCIN IN MICE

In this study, the efficacy of M139603 was tested at 30 ppm and that of salinomycin at 30, 40 or 60 ppm feed. The mouse-groups and test-procedures were similar to those applied under Example 2 above. The results are given in Table 3. Compound M139603 suppressed the infection. Salinomycin failed to do so, even at 60 ppm.

EXAMPLE 4

COMPARATIVE EFFICACY OF M139603 AND LASALOCID IN MICE

In this study, the efficacy of M139603 was tested at 20 ppm feed and that of lasalocid (Hoffman la Roche) at 20, 40 and 80 ppm. The test procedures were similar to those above except for the size of the inoculum of *T.hyodysenteriae* ($1.2 \times 10^7$ cfu) used in infecting each mouse. The results are given in Table 4. Despite use of high inocula, M139603 at 20 ppm completely suppressed the infection in two mice and markedly reduced the *T.hyodysenteriae* populations in the other three placed on this drug. The mean ($\log_{10}$) counts of viable treponemes found in the caecal contents of the various groups were: 2.5 cfu/g caecum (139603 at 20 ppm), 7.35 cfu (lasalocid at 20 ppm), 7.45 cfu (lasalocid at 40 ppm), 3.81 cfu (lasalocid at 80 ppm) and 8.50 cfu (unmedicated control). Thus the efficacy of M139803 at 20 ppm could be considered greater than that of lasalocid at 80 ppm.

EXAMPLE 5

EFFICACY OF M139603 IN PREVENTING SWINE DYSENTERY IN PIGS (EXPERIMENTAL INFECTION)

The efficacy of M139603 was tested at 25 ppm feed.

In this studY two groups (Gp.1 and Gp.2) of pigs, six per group, were experimentally infected with a pathogenic strain of *T. hyodysenteriae* (P18a, IRAD(Institute for Animal Health), Compton, Berks, U.K.) by oro-gastric inoculation of 50 ml of a culture suspension ($1 \times 10^7$ cfu/ml) of the organism into each animal. From post-infection day (PID) to PID 35 the animals in Gp. 1 were offered ad lib a feed comprising "Kwikwean" meal (Rank, Hovis, McDougall Research Ltd; containing no antibiotics) incorporated with M139603 at 25 ppm. Gp.2 remained on unmedicated feed throughout the trial. Drug efficacy was measured primarily on the basis of the number of diarrhoea or dysentery days in relation to pig-days within a group and on the average daily weight gain per pig, in each group over the period of the trial. The daily gain was calculated by dividing group gain at end of trial (PID 35) by the total number of pig-days from PID 1 to PID 35. The results, summarised in Table 5, point to the efficacy of M139603 at 25 ppm feed (which provides for a daily drug intake between 1.25-1.55 mg/kg body-weight) in preventing or minimising the incidence of swine dysentery. In the experiment the pigs were exposed to high infective doses of the organism a day before the introduction of the drug. Under normal circumstances preventive dose-regimes are applied on animals at risk and not on those already infected.

EXAMPLE 6

EFFICACY OF M139603 IN PIGS (NATURAL INFECTION)

In this study, eighteen pigs were allocated to three equal groups (Gp.1-3). Feed incorporated with the drug at 25 or 15 ppm was offered to Gp.1 and 2, respectively, on thirty-eight consecutive days commencing six hours pre-infection. Gp.3 remained on unmedicated feed throughout the trial. The pigs were infected with *T. hyodysenteriae* (strain "P18a") using methods and materials similar to those applied in Example 5. However, seven days following this exposure (post-infection day 7), over a period of seven consecutive days, the pigs in Gp. 1 and 2 were allowed to co-mingle for about two hours each day with some dysenteric "seeder pigs" in a nearby pen. Drug efficacy, as in Example 6, was assessed primarily on the basis of the total number of diarrhoea/dysentery days per group and on the basis of average daily weight gain per pig per group. The findings are summarised in Table 6. The results are indicative of the good efficacy of M139603 even at a level as low as 15 ppm feed in preventing swine dysentery. At this dose-level, the daily drug-intake is unlikely to be more than 0.9 mg/kg/body-weight, if daily feed is calculated at 6% of a pig's body-weight. The diarrhoea score of 6.1% against Gp.1 (25 ppm feed) was result of one of the six animals in group developing a transient dysentery. This result cannot be considered discouraging, since preventive dose regimes with commercially available anti-swine dysentery drugs have not always suppressed the infection.

EXAMPLE 7

EFFICACY OF M139603 IN PIGS AT LOW DOSES

In this experiment twenty-four pigs were split into four equal groups (Gp. 1-4). Gp. 1 and 2 were offered the drug at 15 or 10 ppm feed on forty-two consecutive days, commencing six hours pre-infection. Gp. 3 (infected) and Gp. 4 (uninfected) remained on unmedicated feed throughout. The infection procedures with *T. hyodysenteriae* (P18a) were similar to those applied above. Only three groups, Gp. 1, 2 and 3 were infected. Gp. 4 remained uninfected in a well-isolated pen throughout the trial period. Three days following the initial exposure to the infection (post-infection day 3), over a period of five continuous days, the pigs in Gp. 1, 2 and 3 were allowed to co-mingle with dysenteric "seeder pigs" housed in a separate pen. Drug efficacy was measured using the criteria applied in the Examples 5 and 6. The results are summarised in Table 7. Significant weight gain differences, by post-infection day 21, were found between the medicated (Gp.1 and 2) and the unmedicated, infected group (Gp. 3). Thereafter, the differences narrowed, primarily due to the placement of Gp. 3 on tiamulin to prevent further weight losses, and consequent deaths. Despite the number of diarrhoea days observed for Gp. 1 (6.8%) and Gp. 2 (11.9%) during the forty-two days of medication, the average daily weight-gain per pig on each of these two groups exceeded that recorded for pigs in the uninfected, unmedicated group (GP. 4).

EXAMPLE 8:

The in vitro and in vivo inhibitory activity of 15 semi-synthetic analogues of M139603

The fifteen compounds were compounds of Formula (I):

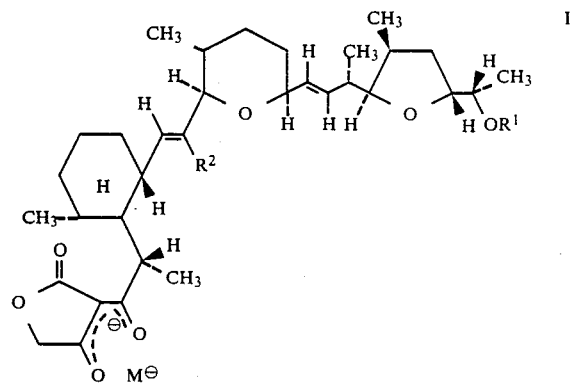

wherein, M+ is sodium, $R^1$ is methyl and $R^2$ is as follows:

| Analogue No | $R^2$ |
| --- | --- |
| 1 | -CH$_2$OMe |
| 2 | -CH$_2$O.COPh |
| 3 | -CH$_2$O.CONHMe |
| 4 | -CH$_2$O.CONH-(4-bromophenyl) |
| 5 | -CH$_2$O.CONH$^n$Bu |
| 6 | -CH$_2$O.CSNHMe |
| 7 | -CH$_2$O.COCH$_2$Br |
| 8 | -CH$_2$O.CO.COOEt |
| 9 | -CH$_2$O.CO(CH$_2$)$^2$COOH |
| 10 | -CH:NOH |
| 11 | -CH$_2$O$^n$Bu |
| 12 | -CH$_2$OCH$_2$-C = CH |
| 13 | -CH$_2$OCH$_2$Ph |
| 14 | -CH$_2$O.COOEt |
| 15 | -CH = N-N(H)-(2,4-dinitrophenyl) |

*T. hyodysenteriae* strain "P18a" was used in both in vitro and in vivo tests as above.

Minimum inhibitory concentration test: An agar-dilution M.I.C. test procedure was applied in the study. The susceptibility of the bacterial strain was tested against a range of dilutions (0.3 mg; 0.1 mg; 0.03 mg; 0.01 mg and 0.003 mg/l medium) of each compound incorporated in plates of Isosensitest agar (Oxoid CM471) with 5% added sheep-blood. The plates, 'spot-inoculated' (Steer's type multipoint inoculator) with a standard culture-suspension of the test strain, were incubated anaerobically at 39° C. for 48-72 hours before reading the results. The M.I.C. of each compound was read as the lowest concentration yielding no growth (no haemolysis) or a hazy growth (faint haemolysis) on the site of the spot-inoculation. The results are shown in Table 8.

In vivo test in mice: this test was similar to that described in Example 2 above, except that approximately 25g mice were infected with 1.0×10$^7$ cfu/ml of P18a and the mice were killed at Day 4 post-infection. Drug efficacy was scored as "good", "moderate" or "inactive" if 80%-100%, 40%-60%, and <40% respectively of individuals in a treated group yielded less than $1.0 \times 10^2$ cfu/g of caecal contents. The results are shown in Table 9.

TABLE 1

Minimum inhibitory concentration (MIC) values of M139603 against *T. hyodysenteriae* in comparison with salinomycin and dimetridazole.

| ISOLATE NO. | MIC µg/ml of | | |
|---|---|---|---|
| | M139803 | SALINOMYCIN | DIMETRIDAZOLE |
| S82/6 | 0.2 | 0.75 | 30 |
| S82/7 | 0.2 | 0.75 | 30 |
| S83/1 | <0.1 | 0.75 | 30 |
| S83/2 | 0.5 | 1.0 | 3.0 |
| S83/5 | <0.1 | <0.1 | 3.0 |
| S85/1 | 0.2 | 0.75 | 30 |

TABLE 1-continued

Minimum inhibitory concentration (MIC) values of M139603 against *T. hyodysenteriae* in comparison with salinomycin and dimetridazole.

| ISOLATE NO. | MIC µg/ml of | | |
|---|---|---|---|
| | M139803 | SALINOMYCIN | DIMETRIDAZOLE |
| S85/2 | 0.2 | 1.0 | 10 |
| S85/3 | 0.2 | 0.75 | 10 |
| S85/8 | 0.2 | 0.75 | 3.0 |
| S85/9 | <0.1 | 0.5 | 5.0 |
| S86/1 | <0.1 | <0.1 | <0.5 |
| S86/2 | 0.2 | 0.75 | 10 |
| B78 | 0.5 | 1.0 | 3.0 |
| Mean (13 strains) | 0.215 | 0.68 | 12.88 |

TABLE 2

Activity of M139803 in comparison with monensin against *T.hyodysenteriae* in experimentally infected mice

| GROUP | MOUSE NO. | DRUG | DOSE-LEVEL (ppm. feed) | MEDICATION PERIOD | VIABLE TREPONEMES PER GRAM CAECUM & CONTENTS |
|---|---|---|---|---|---|
| 1 | 1 | M-139603 | 25 ppm | 5 days | negative** |
| | 2 | M-139603 | 25 ppm | 5 days | negative** |
| | 3 | M-139603 | 25 ppm | 5 days | negative** |
| | 4 | M-139603 | 25 ppm | 5 days | negative** |
| | 5 | M-139603 | 25 ppm | 5 days | negative** |
| | Mean ($\log_{10}$) | | | | 0 |
| 2 | 1 | Monensin | 50 ppm | 5 days | $1.74 \times 10^8$ |
| | 2 | Monensin | 50 ppm | 5 days | $2.90 \times 10^7$ |
| | 3 | Monensin | 50 ppm | 5 days | $1.0 \times 10^5$ |
| | 4 | Monensin | 50 ppm | 5 days | negative |
| | 5 | Monensin | 50 ppm | 5 days | $2.0 \times 10^5$ |
| | Mean ($\log_0$) | | | | 5.2 |
| 3 | 1 | Monensin | 100 ppm | 5 days | negative** |
| | 2 | Monensin | 100 ppm | 5 days | negative** |
| | 3 | Monensin | 100 ppm | 5 days | negative** |
| | 4 | Monensin | 100 ppm | 5 days | negative** |
| | 5 | Monensin | 100 ppm | 5 days | negative** |
| | Mean ($\log_{10}$) | | | | 0 |
| 4 | 1 | Unmedicated | — | 5 days | $1.01 \times 10^8$ |
| | 2 | Unmedicated | — | 5 days | $3.2 \times 10^7$ |
| | 3 | Unmedicated | — | 5 days | $5.0 \times 10^6$ |
| | 4 | Unmedicated | — | 5 days | $3.28 \times 10^8$ |
| | 5 | Unmedicated | — | 5 days | $>9.9 \times 10^8$ |
| | Mean ($\log_{10}$) | | | | 7.94 |

**Limit of detection = $<1.0 \times 10^2$

TABLE 3

Activity of M139603 in comparison with salinomycin against *T. hyodysenteriae* in experimentally infected mice.

| GROUP | MOUSE NO. | DRUG | DOSE LEVEL (ppm feed) | MEDICATION PERIOD | VIABLE TREPONEMES PER GRAM CAECUM & CONTENTS |
|---|---|---|---|---|---|
| 1 | 1 | M139603 | 30 ppm | 5 days | negative |
| | 2 | M139603 | 30 ppm | 5 days | negative |
| | 3 | M139603 | 30 ppm | 5 days | negative |
| | 4 | M139603 | 30 ppm | 5 days | negative |
| | 5 | M139603 | 30 ppm | 5 days | negative |
| | Mean ($\log_{10}$) | | | | 0 |
| 2 | 1 | Salinomycin | 30 ppm | 5 days | negative |
| | 2 | Salinomycin | 30 ppm | 5 days | negative |
| | 3 | Salinomycin | 30 ppm | 5 days | $6.0 \times 10^6$ |
| | 4 | Salinomycin | 30 ppm | 5 days | $6.0 \times 10^6$ |
| | 5 | Salinomycin | 30 ppm | 5 days | $5.4 \times 10^5$ |
| | Mean | | | | |

TABLE 3-continued

Activity of M139603 in comparison with salinomycin against *T. hyodysenteriae* in experimentally infected mice.

| GROUP | MOUSE NO. | DRUG | DOSE LEVEL (ppm feed) | MEDICATION PERIOD | VIABLE TREPONEMES PER GRAM CAECUM & CONTENTS |
|---|---|---|---|---|---|
| | | | | | ($\log_{10}$) 3.86 |
| 3 | 1 | Salinomycin | 40 ppm | 5 days | $6.0 \times 10^6$ |
| | 2 | Salinomycin | 40 ppm | 5 days | $1.8 \times 10^6$ |
| | 3 | Salinomycin | 40 ppm | 5 days | $1.6 \times 10^5$ |
| | 4 | Salinomycin | 40 ppm | 5 days | $1.8 \times 10^6$ |
| | 5 | Salinomycin | 40 ppm | 5 days | $4.3 \times 10^5$ |
| | Mean ($\log_{10}$) | | | | 6.03 |
| 4 | 1 | Salinomycin | 60 ppm | 5 days | $1.3 \times 10^7$ |
| | 2 | Salinomycin | 60 ppm | 5 days | $2.0 \times 10^4$ |
| | 3 | Salinomycin | 60 ppm | 5 days | $1.0 \times 10^6$ |
| | 4 | Salinomycin | 60 ppm | 5 days | $1.0 \times 10^4$ |
| | 5 | Salinomycin | 60 ppm | 5 days | $1.5 \times 10^6$ |
| | Mean ($\log_{10}$) | | | | 5.52 |
| 5 | 1 | Unmedicated | — | 5 days | $4.3 \times 10^6$ |
| | 2 | Unmedicated | — | 5 days | $2.0 \times 10^7$ |
| | 3 | Unmedicated | — | 5 days | $4.0 \times 10^7$ |
| | 4 | Unmedicated | — | 5 days | $1.9 \times 10^5$ |
| | 5 | Unmedicated | — | 5 days | $2.1 \times 10^7$ |
| | Mean ($\log_{10}$) | | | | 6.83 |

TABLE 4

Activity of M139603 in comparison with lasalocid against *T. hyodysenteriae* in experimentally infected mice

| GROUP | MOUSE NO | DRUG | DOSE-LEVEL (ppm. feed) | MEDICATION PERIOD | VIABLE TREPONEMES PER GRAM CAECAL CONTENTS |
|---|---|---|---|---|---|
| 1 | 1 | M139603 | 20 ppm | 5 days | 0 |
| | 2 | M139603 | 20 ppm | 5 days | $4.3 \times 10^3$ |
| | 3 | M139603 | 20 ppm | 5 days | 0 |
| | 4 | M139603 | 20 ppm | 5 days | $3.0 \times 10^2$ |
| | 5 | M139603 | 20 ppm | 5 days | $1.0 \times 10^2$ |
| | Mean ($\log_{10}$) | | | | 1.62 |
| 2 | 1 | Lasalocid | 20 ppm | 5 days | $3.2 \times 10^8$ |
| | 2 | Lasalocid | 20 ppm | 5 days | $1.1 \times 10^4$ |
| | 3 | Lasalocid | 20 ppm | 5 days | $3.2 \times 10^8$ |
| | 4 | Lasalocid | 20 ppm | 5 days | $2.9 \times 10^7$ |
| | 5 | Lasalocid | 20 ppm | 5 days | $1.7 \times 10^8$ |
| | Mean ($\log_{10}$) | | | | 7.35 |
| 3 | 1 | Lasalocid | 40 ppm | 5 days | $3.0 \times 10^6$ |
| | 2 | Lasalocid | 40 ppm | 5 days | $1.4 \times 10^8$ |
| | 3 | Lasalocid | 40 ppm | 5 days | $2.1 \times 10^8$ |
| | 4 | Lasalocid | 40 ppm | 5 days | $1.7 \times 10^7$ |
| | 5 | Lasalocid | 40 ppm | 5 days | $1.2 \times 10^7$ |
| | Mean ($\log_{10}$) | | | | 7.45 |
| 4. | 1 | Lasalocid | 80 ppm | 5 days | $4.0 \times 10^4$ |
| | 2 | Lasalocid | 80 ppm | 5 days | 0 |
| | 3 | Lasalocid | 80 ppm | 5 days | $1.0 \times 10^6$ |
| | 4 | Lasalocid | 80 ppm | 5 days | $1.3 \times 10^5$ |
| | 5 | Lasalocid | 80 ppm | 5 days | $2.3 \times 10^3$ |
| | Mean ($\log_{10}$) | | | | 3.81 |
| 5 | 1 | Lasalocid Unmedicated | | 5 days | $4.4 \times 10^8$ |
| | 2 | Lasalocid Unmedicated | | 5 days | $1.1 \times 10^8$ |
| | 3 | Lasalocid Unmedicated | | 5 days | $7.2 \times 10^8$ |
| | 4 | Lasalocid Unmedicated | | 5 days | $2.5 \times 10^8$ |
| | 5 | Lasalocid Unmedicated | | 5 days | $3.4 \times 10^8$ |
| | Mean ($\log_{10}$) | | | | 8.50 |

TABLE 5
Summary of results of experiment at 25 ppm feed.

|  | Group 1 Medicated | Group 2 Unmedicated |
|---|---|---|
| Number pigs/group | 6 | 6 |
| Drug in feed (ppm) | 25 | 0 |
| Period (days) of continuous daily medication commencing 24 hour post-infection | 35 | |
| Ave. daily drug-intake (mg/kg body-wt) based on | | |
| (i) ave daily feed-intake at 5% animal's body-wt. | 1.25 | 0 |
| (ii) ave daily feed-intake at 6% animal's body-wt. | 1.5 | 0 |
| Mortality (+ culls) | 0 | 2 |
| Number diarrhoea/dysentery days (PID 1-35) | 27 | 75 |
| Percent diarrhoea/dysentery days (PID 1-35) | 12.9 | 46.3 |
| Group weight (kg) at start of experiment | 112 | 108.5 |
| Average weight at start of experiment | 18.8 | 18.1 |
| Group weight (kg) at termination | 243 | 137 |
| Average weight at termination | 40.5 | 34.25 |
| Number pigs days at termination | 210 | 162 |
| Averae daily weight-gain (kg) | 0.62 | 0.17 |

TABLE 6
Summary of results of experiment at 15 or 25 ppm feed

|  | Group 1 | Group 2 | Group 3 |
|---|---|---|---|
| Number pigs/group | 6 | 6 | 6 |
| Drug in feed (ppm) | 25 | 15 | 0 |
| No. days medication commencing 6 hrs pre-infection | 38 | 38 | 0 |
| Ave. daily drug-intake (mg/kg body-wt), based on | | | |
| (i) ave daily feed-intake at 5% animal's body-wt. | 1.25 | 0.75 | 0 |
| (ii) ave daily feed-intake at 6% animal's body-wt. | 1.5 | 0.9 | 0 |
| Mortality (+ culls) | 0 | 0 | 1 |
| Number diarrhoea/dysentery days (pi 1 to 38) | 14 | 0 | 81 |
| Percent diarrhoea/dysentery days (pi 1 to 38) | 6.1 | 0 | 37.9 |
| Group weight (kg) at start: day 3 pre-infecton | 65.7 | 65.5 | 65.1 |
| Average weight (kg) at day 3 pre-infection | 10.95 | 10.95 | 10.85 |
| Group weight (kg) at end | 246.5 | 246.5 | 158 |
| Average weight (kg) at end | 41.0 | 41.0 | 26.3 |
| Number pig days at end | 228 | 228 | 214 |
| Average daily weight-gain (kg) | 0.72 | 0.72 | 0.39 |

TABLE 7
Summary of results of experiment at 10 or 15 ppm

|  | GROUP 1 | GROUP 2 | GROUP 3 | GROUP 4 |
|---|---|---|---|---|
| No. pigs/group | 6 | 6 | 6 | 6 |
| Drug in feed (ppm) | 15 | 10 | 0 | 0 |
| Average daily drug intake mg/kg body-wt.) based on:- | | | | |
| (i) ave. daily feed intake at 5% body-weight | 0.75 | 0.5 | 0 | 0 |
| (ii) ave. daily feed intake at 6% body-weight | 0.90 | 0.6 | 0 | 0 |
| Mortality (+ culls) | 0 | 0 | 0 | 0 |
| No. diarrhoea/dysentery days days from:- | | | | |
| (i) post-infection day 1 to 21 (126 pig-days) | 5 | 6 | 66 | 0 |
| (ii) post-infection day 1 to 42 (252 pig-days) | 17 | 30 | NA | 0 |
| Percent diarrhoea/dysentery days from:- | | | | |
| (i) post-infection day 1 to 21 | 4 | 4.8 | 2.4 | 0 |
| (ii) post-infection day 1 to 42 | 6.8 | 11.9 | NA | 0 |
| Group weight at start (day 4 pre-infection) | 63.7 | 66.0 | 64.0 | 63.2 |
| Ave. weight at start (day 4 pre-infection) | 10.6 | 11.0 | 10.7 | 10.5 |
| Group weight on:- | | | | |
| (i) post-infection day 21 | 153.7 | 161.0 | 76.4 | 151.8 |
| (ii) post-infection day 43 (1 day from withdrawal of medication) | 225.5 | 265.0 | 181.0 | 250.9 |
| (iii) post-infection day 57 (15 days from withdrawal of medication) | 327.5 | 319.5 | 248.5 | 337.5 |
| No. pig days from | | | | |
| (i) pre-infection day 4 to post-infection day 22 | 162 | 162 | 162 | 162 |
| (ii) post-infection day 23 to 43 | 258 | 258 | 258 | 258 |
| (iii) post-infection day 44 to 57 | 342 | 342 | 342 | 342 |
| Ave. daily weight-gain from:- | | | | |
| (i) day 4 pre-infection to day 22 post-infection | 0.56 | 0.59 | 0.08 | 0.55 |
| (ii) post-infection day 23 to 43, inclusive | 0.81 | 0.83 | 0.83 | 0.79 |
| (iii) post-infection day 44 to 57, inclusive | 0.86 | 0.65 | 0.80 | 1.03 |

Explanatory: NA = Not Applicable. Group was placed on tiamulin treatment from post-infection day 22-26

TABLE 8

| COMPOUND | M.I.C. (mg/l) |
|---|---|
| M139603 | 0.01 |
| Analogue 1 | 0.03 |
| Analogue 2 | 0.01 |
| Analogue 3 | 0.1 |
| Analogue 4 | 0.03 |
| Analogue 5 | 0.03 |
| Analogue 6 | 0.03 |
| Analogue 7 | 0.03 |
| Analogue 8 | 0.003 |
| Analogue 9 | >0.03 |
| Analogue 10 | 0.01 |
| Analogue 11 | 0.01 |
| Analogue 12 | 0.003 |
| Analogue 13 | 0.01 |
| Analogue 14 | 0.03 |
| Analogue 15 | >0.3 |

TABLE 9

| Compound | Drug-level (ppm feed) | Activity |
|---|---|---|
| Analogue 1 | 20 | good |
| Analogue 2 | 10 | inactive |
|  | 20 | good |
| Analogue 8 | 10 | moderate |
|  | 20 | moderate |
| Analogue 10 | 10 | moderate |
|  | 20 | moderate |
| Analogue 12 | 10 | moderate |
|  | 12 | active |
|  | 20 | active |
|  | 24 | active |

What is claimed is:

1. A method of combatting a *Treponema hyodysenteriae* infection in a pig having said infection comprising orally administering to a pig having said infection an effective infection combatting amount of tetronasin or physiologically acceptable salt thereof.

2. A method of preventing a *Treponema hyodysenteriae* infection in a pig in need thereof, which comprises orally administering to said pig an effective *Treponema hyodysenteriae* infection prevention amount of tetronasin or physiologically acceptable salt thereof.

3. A method of combatting a *Treponema hyodysenteriae* infection in a pig, which comprises the suitable oral administration to a pig in need thereof of an effective amount of the compounds of formula (I):

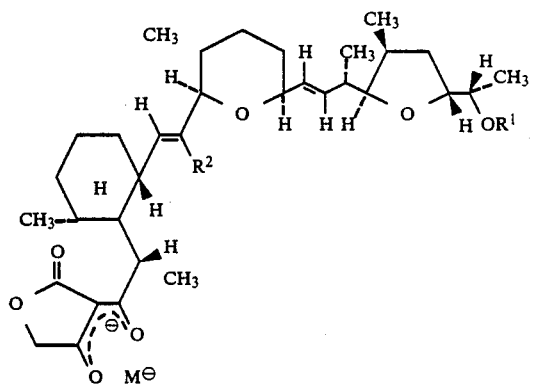

wherein:
M+ is an alkali metal, alkaline earth metal, ammonium, alkylammonium or hydroxyalkylammonium cation;

$R^1$ is a hydrogen atom, an alkyl radical or an optionally substituted phenylalkyl radical; and is a formyl, iminomethyl, hydroxyiminimethyl or aminomethyl radical, or a radical of the formula —CH:$NR^3$, —CH:$NOR^4$ or —CH$_2$$NR^5R^6$ wherein $R^3$, $R^4$, $R^5$ and $R^6$ may each be an alkyl or an optionally substituted phenyl or phenylalkyl radical;

or a radical of the formula —CH$_2$O$R^7$ wherein $R^7$ is an alkyl, alkenyl, alkynyl, alkoxycarbonyl or alkylaminoalkyl radical or an optionally substituted phenylalkyl radical; or a radical of the formula —CH$_2$O.CO$R^8$ wherein $R^8$ is an alkyl, cycloalkyl, (cycloalkyl)alkyl, halogenoalkyl, hydroxyalkyl, alkoxyalkyl, aminoalkyl, mono- or di-alkylaminoalkyl, alkoxycarbonylalkyl, carboxyalkyl, carbamoylalkyl, N-alkylcarbamoylalkyl, N,N-dialkylcarbamoylalkyl or optionally substituted phenyl, naphthyl or phenylalkyl radical; or a radical of the formula —CH$_2$O.CO.CO$R^9$ is an amino, mono- or di-alkylamino, alkoxy or optionally substituted phenyl, naphthyl or phenylalkyl radical; or a radical of the formula —CH$_2$O.CX.NR$^{10}$R$^{11}$ wherein X is an oxygen or sulphur atom and R$^{10}$ and R$^{11}$, which may be the same or different, are each a hydrogen atom, an alkyl radical or an optionally substituted phenyl, naphthyl or phenylalkyl radical;

or, when $R^1$ is a hydrogen atom or an alkyl radical of 2 or more carbon atoms or an optionally substituted phenylalkyl radical, $R^2$ is a hydroxymethyl radical, and wherein each alkyl, alkenyl or alkynyl radical contains up to 6 carbon atoms, and wherein, in each complex radical containing an alkyl part, the said alkyl part contains 1 to 6 carbon atoms, and wherein each cycloalkyl radical or cycloalkyl part of a (cycloalkyl)-alkyl radical contains 3 to 7 carbon atoms and wherein the optional substituent in the optionally substituted phenyl, naphathyl or phenylalkyl radical is a halogen atom, a nitro, cyano or hydroxy radical, or an alkyl, alkoxy, halogenoalkyl, halogenoalkoxy, alkylamino, dialkylamino or alkanoylamino radical of up to 8 carbon atoms.

* * * * *